United States Patent [19]

Thir et al.

[11] Patent Number: 4,568,480

[45] Date of Patent: Feb. 4, 1986

[54] MICROEMULSIONS

[75] Inventors: Basil Thir; Edward M. Dexheimer, both of Grosse Ile, Mich.

[73] Assignee: BASF Wyandotte Corporation, Wyandotte, Mich.

[21] Appl. No.: 552,643

[22] Filed: Nov. 17, 1983

[51] Int. Cl.[4] .................. A01N 61/02; B01J 13/00; C07C 41/00

[52] U.S. Cl. .................. 252/312; 260/410.6; 568/609; 252/309; 252/351; 252/DIG. 1; 252/DIG. 14; 514/939; 252/174.21

[58] Field of Search .................. 252/312, 309, 8.55 D, 252/351; 568/609; 260/410.6

[56] References Cited

U.S. PATENT DOCUMENTS

| | | | |
|---|---|---|---|
| 2,178,851 | 11/1939 | Bruson | 568/609 X |
| 2,630,457 | 3/1953 | Hansen et al. | 252/312 |
| 2,759,867 | 8/1956 | Melass | 568/609 X |
| 3,024,198 | 3/1962 | Harrington et al. | 252/312 |
| 3,577,340 | 5/1971 | Paviak et al. | 252/312 |
| 3,699,173 | 10/1972 | Osberg et al. | 568/609 |
| 3,706,708 | 12/1972 | Kearnan | 252/309 X |
| 3,799,956 | 3/1974 | Nakamura et al. | 252/351 X |
| 3,829,508 | 8/1974 | Diery et al. | 252/351 X |
| 3,935,123 | 1/1976 | Prokai et al. | 252/351 |
| 3,998,754 | 12/1976 | Oswald | 252/351 |
| 4,208,301 | 6/1980 | Gammon | 252/358 X |
| 4,258,448 | 3/1981 | Reitz et al. | 252/312 X |
| 4,360,452 | 11/1982 | Zabrocki et al. | 252/312 X |

FOREIGN PATENT DOCUMENTS 882623 11/1961 United Kingdom ............... 568/609

OTHER PUBLICATIONS

The Chemistry and Manufacture of Cosmetics, 2nd Ed., vol. III, p. 32, by Maison de Navarre.

*Primary Examiner*—Richard D. Lovering
*Assistant Examiner*—Catherine S. Kilby
*Attorney, Agent, or Firm*—Bernhard R. Swick

[57] ABSTRACT

A microemulsion of water and an alkoxylated phenol derivative which may also contain an oil and an additional surfactant.

20 Claims, No Drawings

MICROEMULSIONS

BACKGROUND OF THE INVENTION

1. Field of the Invention

This invention relates to microemulsions suitable for use in many applications such as fragrances, cleaning fluids, paint vehicles, toxicants and antiseptics, cosmetics and toiletries, and foods and flavors and pharmaceuticals.

2. Description of the Prior Art

A microemulsion is an extraordinary kind of emulsion that forms spontaneously. Products consisting of these systems are prized for their stability and small particle size, which gives them special consideration in the marketplace.

Microemulsions are stable dispersions of one liquid in another in the form of droplets, the diameter of which are less than one-quarter the wave length of white light. Although this size requirement means that light can pass through it, the system is not necessarily transparent. It is generally referred to as translucent which term is defined to include "transparency," which may be described as excellent translucency. Such systems remain dispersed and will not as macroemulsions do, achieve equilibrium by separating into the original, mutually insoluble liquid phases. While with the aid of surfactants, it is possible to produce macroemulsions which remain dispersed for periods of time as long as 24 hours or possibly more, ultimately they achieve equilibrium by separating into the original, mutually insoluble liquid phases. On the other hand, microemulsions exhibit stability which may be measured in years. Historically such systems have been referred to as "solubilized" rather than considered to be emulsions.

Microemulsions are recognized by the physical properties displayed by their small droplets. The optical properties of these micro droplets and their behavior in a gravitational field easily differentiate them from macro droplets.

Microemulsions are particularly useful and in some cases essential as compared to macroemulsions for many applications. For example, it is often desirable to emulsify water-insoluble fragrances for mouthwashes, shaving lotions, or similar products in order to prevent them from precipitating out of the alcohol-water mixtures in cold weather. Microemulsification in transparent form is essential to maintain the "polished" clarity of these products. Also, water-in-oil emulsions of cleaning fluids make it possible for dirt and stains to be exposed to both liquids during the cleaning operation. Microemulsions increase the efficiency of the mixture and prolong its life. Possibly the largest single use of microemulsions is in the paint industry. Many paint vehicles are oil-in-water microemulsions of alkyds or polymers. The stability of these vehicles insures uniformity of application and coherent films. The small particle size of the microemulsions enables high gloss finishes to be easily formulated. The use of water instead of smelly and noxious solvents has enormous consumer appeal and in industrial use saves money on fire insurance premiums and reduces air pollution.

Many products in the cosmetic and toiletries area, such as cold creams, shampoos, etc., are microemulsions. Usually, they are used to insure stablity or transparency, but frequently advantage is taken of the light scattering properties (translucency or opalescence) of micro droplets to appeal to the consumer. Microemulsions of water-insoluble materials are utilized in the food industry primarily to meet stringent stability requirements. Any breakdown of the emulsion during storage or shipment with consequent deterioration of appearance could be disastrous. For this reason, transparent systems with large excesses of edible emulsifiers are usually employed. Microemulsions of flavor oils in cola, cream soda, and other confections are typical examples.

Many drugs are insoluble in water, but it is desirable for one reason or another to administer them in an aqueous medium. Where accurate dosage is required so that uniformity of dispersion is essential, microemulsification is indicated. In the case of consumer items for oral ingestion, (e.g., vitamin oils), the transparency of a stable microemulsion has sales appeal.

While there is a strong need for microemulsions, as is evident from the previous discussion, unfortunately producing such emulsions is often difficult, if not impossible. It is generally necessary to test a wide variety of surfactants to try to achieve such microemulsion in a wide variety of chemical types as stated in *Emulsions and Emulsion Technology*, part 1, by Kenneth J. Lissant, published by Marcel Dekker, Inc., New York, 1974, page 167, which says, "Although this method of finding a microemulsifier is a workable one, it is obviously time-consuming and its chances of success *without a great many experiments* are small." (Emphasis added.)

SUMMARY OF THE INVENTION

In accordance with the instant invention, it has been surprisingly discovered that microemulsions with water can be prepared using a fatty acid ester of alkoxylated phenol derivatives as a microemulsifier. These compounds are self-emulsifiers. However, they are particularly useful for difficult to produce microemulsions with water and oils for mouthwashes, shaving lotions, etc., cleaning fluids, paint vehicles, textile auxiliaries, cosmetics and toiletries, foods and flavors, and pharmaceuticals. While not essential to produce microemulsions, such microemulsions may also contain additional components such as salts of alkoxylated phosphate esters. The microemulsions of this invention generally comprise by weight about 5 to 70 percent, preferably 10 to 30 percent, of the alkoxylated phenol derivative ester, about 30 to 95 percent water, 0 to about 40 percent of the desired oil, and 0 to about 40 percent of any additional components such as the salt of an alkoxylated phosphate ester.

The fatty acid ester of alkoxylated phenol derivatives comprises a compound selected from the group consisting of

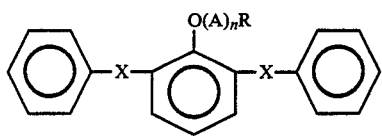

(I)

-continued

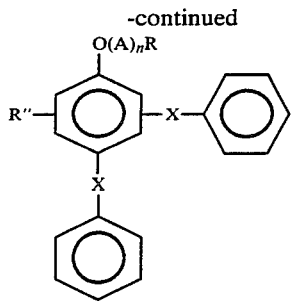
(II)

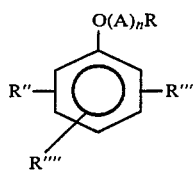
(III)

and

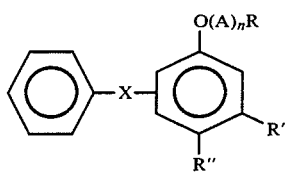
(IV)

wherein A is an oxyalkylene radial having 2 carbon atoms to 4 carbon atoms or mixtures thereof, R is acyl containing from 8 carbon atoms to 22 carbon atoms, R' is alkyl containing from 1 carbon atom to 10 carbon atoms, R" is alkyl containing from 1 carbon atom to 22 carbon atoms, R'" is alkyl containing from 4 carbon atoms to 8 carbon atoms and R"" is R" or R'", X is an alkylidene radical containing from 1 carbon atoms to 3 carbon atoms and n is an integer such that the molecular weight of the compound is between 500 and 2500 and with the proviso that either R" or R'" is ortho to the oxygen in formula III. In preferred embodiments the oxyalkylene radical is oxyethylene or a mixture of oxyethylene and up to 50 percent by weight of an oxyalkylene radical having 3 carbon atoms to 4 carbon atoms and provides effective hydrophilicity to the compound to enable it to self emulsify in water.

DESCRIPTION OF THE PREFERRED EMBODIMENTS

The esters employed in the present invention are prepared from three essential ingredients, i.e., certain phenol derivatives, alkylene oxides and fatty acids.

Useful as the phenol derivatives are compounds selected from the group consisting of the following formulas:

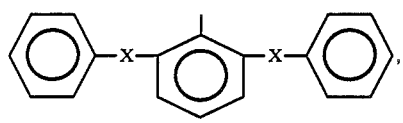
(V)

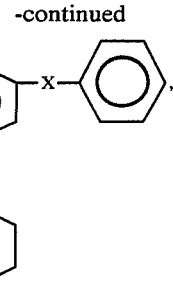
(VI)

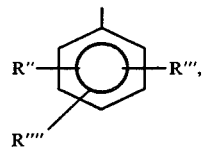
(VII)

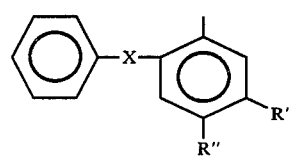
(VIII)

wherein X, R', R", R'" and R"" are as described above. Examples of X are alkylidene radicals such as methylene, ethylene and propylidene. Examples of R' and R" are methyl and isobutyl. Examples of R'" and R"" are butyl and octyl. Preferably used as the phenol derivative of formula V is a compound wherein X is

, as the phenol derivative of formula VI is a compound wherein X is

as the phenol derivative of formula VII is a compound wherein R" is $C_4H_9-$, R'" is $C_8H_{17}-$ and R"" is $C_8H_{17}-$ or $C_4H_9-$ or a compound wherein R" is $C_4H_9-$, R'" is $C_4H_9-$ and R"" is $CH_3-$ and as the phenol derivative of formula VIII is a compound wherein X is

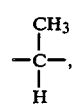,

R' is $CH_3-$ and R" is $C_4H_9-$.

Useful as alkylene oxides, from which the oxyalkylene radical derives, are alkylene oxides containing 2 carbon atoms to 4 carbon atoms such as ethylene oxide, propylene oxide and butylene oxide. Useful in a preferred embodiment is ethylene oxide or a mixture of ethylene oxide and other alkylene oxides which when used in a mixture with ethylene oxide impart a hydrophilicity effective to self emulsify the compound. In lieu of the other alkylene oxides, other 3 or 4-carbon cyclic ethers such as tetrahydrofuran, oxetane, and methyl oxetane may be used. Preferably used are mixtures of ethylene oxide and propylene oxide.

The oxyalkylene is present in an amount, as represented by n of formulas I–IV, such that the molecular weight of the compound is between 500 and 2500. Preferably used in a block of between 5 and 20 moles, such as 5, 10 or 15 moles of ethylene oxide per mole of phenol derivative. Also preferably used is a heteric mixture of about 70 percent by weight oxyethylene and about 30 percent by weight oxypropylene.

Useful as fatty acids are those containing between 8 carbon atoms and 22 carbon atoms, preferably between 16 and 20 carbon atoms and more preferably 18 carbon atoms, such as isostearic acid.

The phenol derivative is ethoxylated by adding the phenol derivative and a basic catalyst to an autoclave evacuated to a vacuum and pressurized with nitrogen and equipped with temperature, pressure and vacuum controls, and thereafter heated. The alkylene oxide is added at a constant rate until all the oxide is added. The reaction then proceeds at a temperature between 90° C. and 130° C. until a constant pressure is observed. Esterification is then accomplished by adding approximately equal molar amounts of fatty acid and alkoxylated phenol derivative. Acid catalysts, such as methane sulfonic acid and hypophosphorus acid are added and the esterification reaction is allowed to proceed at a constant temperature, such as 165° C. under a nitrogen blanket.

The ester compound is particularly useful, and in some cases essential, in preparing microemulsions of various oils for fragrances, cleaning fluids, paint vehicles, toxicants, cosmetics and toiletries, foods and flavors, and pharmaceuticals.

The instant invention may be employed to form water-in-oil and oil-in-water microemulsions from water and oils such as mineral oils, butyl stearate, tridecyl stearate, isotridecyl stearate, soybean oil, coconut oil, corn oil, rapeseed oil, castor oil, various fragrance oils, alkyds of various polymer oils, chlordane, pentachlorophenol, pine oil, various flavoring oils, vitamin oils, etc.

Particularly effective microemulsions are achieved with the further addition or inclusion of alkali metal salts of alkoxylated phosphate esters and of various quaternary compounds. Particularly useful is the sodium or potassium salt of the phosphate ester of an ethoxylated or ethoxylated/propoxylated aliphatic alcohol having from 10 to 18 carbon atoms. The microemulsion composition may also include other and various components depending upon the ultimate product, that is to say, the normal additives and components of the ultimate products such as those found in products such as fragrances, cleaning fluids, paint vehicles, toxicants, cosmetics, flavors, pharmaceuticals, etc. The microemulsions of the instant invention generally comprise about 5 to 70 percent, and preferably about 10 to 30 percent, of the above-described ester compound, about 30 to 95 percent water, 0 to about 40, preferably about 1 to 30, percent oil, and 0 to about 40, preferably about 1 to 40, percent alkali metal salt of an alkoxylated phosphate ester and/or other additives.

While microemulsions may be employed using the above with the ranges of the above set forth proportions, the actual production of a microemulsion requires a certain amount of trial and error of proportions within the above ranges. More specifically, as pointed out in the above cited Lissant publication, production comprises dissolving one part of the emulsifier in one part of the oil (with heating if necessary) and then an equal volume of water is slowly poured into this mixture. Microemulsions of just the emulsifier, i.e., the above-described ester compound, and water are prepared by merely adding an equal volume of water to an equal volume of the ester compound. If the system does not tolerate this water, the amount of the ester compound should be increased until the system does tolerate water and remains clear or opalescent. If initially the system tolerates water and remains clear or opalescent, a water-in-oil microemulsion has been formed. On further addition of small aliquots of water to this water-in-oil microemulsion an oil-in-water microemulsion will usually form. In this manner, the optimum proportions can be easily determined by one skilled in the art.

The following examples will further illustrate the various aspects of the invention. Where not otherwise specified throughout the specification and claims, temperatures are in the degrees Centigrade, and parts, percentages and proportions are by weight.

EXAMPLE 1

To an autoclave equipped with temperature, pressure, and vacuum controls was added 780 parts of butylated, styrenated cresol (WINGSTAY ® V-Goodyear Company) and 8 parts of 45 percent potassium hydroxide solution. The autoclave was heated to 125° C. after evacuating to a vacuum of less than 10 millimeters mercury and then pressurizing to 35 lbs./square inch with nitrogen. Ethylene oxide was added at a rate of 250 parts/hour until 1921 parts were added. When constant pressure was observed, the catalyst was removed by deionization and the mixture was further stripped to remove volatiles. This ethoxylate, Example 1A, had a hydroxyl number of 66.2 and a viscosity of 883 Saybolt universal seconds at 100° F.

To a 2 liter flask having temperature control, stirrer and distillation apparatus were added 891 parts of the above ethoxylate. Next, 279.1 parts of isostearic acid, 4.12 parts of methanesulfonic acid, (70 percent), and 4.0 parts of hypophosphorous acid were added. The temperature was held at a constant 165° C. in a nitrogen atmosphere until the esterification reaction was complete. After catalyst removal, the product of Example 1 of this invention, the isostearate ester of ethoxylated butylated styrenated cresol, a specific product containing compounds of formula VIII above, was obtained having a hydroxyl number of 4.4, an acid number of 1.56 and a viscosity of 781 Saybolt universal seconds at 100° F.

EXAMPLE 2

Twenty-five parts by weight of the isostearate ester prepared in accordance with Example 1 was added to 12.5 parts of the sodium salt of the phosphate ester of an oxyalkylated alcohol with stirring. The oxyalkylated alcohol was the reaction product of a 10 to 18 carbon atom aliphatic alcohol with a mixture of ethylene oxide and propylene oxide wherein the molecular weight of the oxyalkylene groups is 800 and the percentage of oxyethylene groups is 60 percent. To this mixture was added 12.5 parts by weight of tridecyl stearate followed by 50 parts of water. The mixture was stirred for 30 minutes and allowed to stand. A clear microemulsion was obtained. Dilution of the emulsion with 200 parts of additional water still exhibited the properties of a microemulsion.

EXAMPLE 3

An isostearate ester was prepared by the method of Example 1 with the exception that in lieu of the butylated styrenated cresol, sold by the Goodyear Company under the trademark WINGSTAY V ®, was substituted a commercial product of formula V above (WINGSTAY S, Goodyear Company) wherein X is

A microemuslsion was prepared from this isostearate ester following the procedure of Example 2 above but substituting for the sodium salt of the phosphate ester of Example 2, a potassium salt of a similar phosphate ester but wherein the molecular weight of the oxyalkylene groups is 830 and the percent oxyethylene groups is 25 percent. A clear microemulsion was obtained which even when diluted with 100 additional parts of water still maintained the properties of a microemulsion.

EXAMPLE 4

Fifty parts by weight of the isostearate ester of Example 3 was added to 50 parts by weight of the sodium salt of the phosphate ester of Example 12 with stirring. To this mixture were added 50 parts by weight of water. The mixture was stirred for 30 minutes and allowed to stand. A clear microemulsion was obtained. This emulsion was diluted further with 150 parts by weight of additional water and still maintained the properties of microemulsion.

EXAMPLE 5

A microemulsion is prepared as described in Example 4 with the exception that the isostearate ester of the ethoxylated product of formula VII above was prepared wherein R'' is $C_4H_9$—, R''' is $C_8H_{17}$— and R'''' is a mixture of $C_4H_9$— and $C_8H_{17}$— (WINGSTAY T-Goodyear Company). A clear microemulsion is obtained which when diluted with 200 parts of additional water still maintains the properties of a microemulsion.

EXAMPLE 6

Example 4 is repeated with the exception that the isostearate ester of ethoxylated product of formula VI above is employed wherein X is

and R'' is $C_4H_9$— (WINGSTAY C-Goodyear Company). A clear emulsion is obtained which emulsion may be diluted with 200 parts of additional water and still maintain the properties of microemulsion.

EXAMPLE 7

Example 4 is repeated with the exception that the laurate ester of Example 1(A) above is substituted for the isostearate ester employed in Example 4. A clear emulsion is obtained. Two hundred parts of additional water are added and the properties of the microemulsion still are retained.

EXAMPLE 8

Example 2 is repeated with the exception that in lieu of the isostearate ester of Example 1 a similar isostearate ester prepared as in Example 1 was substituted wherein in lieu of the 1921 parts of ethylene oxide was added 1921 parts of a mixture of ethylene oxide and propylene oxide having a weight ratio of ethylene oxide to propylene oxide of 70:30.

The embodiments of the invention in which an exclusive priviledge or property is claimed are defined as follows:

1. A microemulsion comprising by weight about 30 to 90 percent water and 10 to 70 percent of a compound selected from the group consisting of:

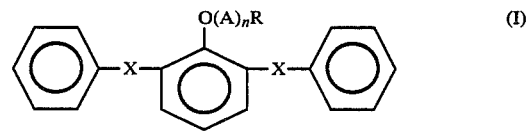

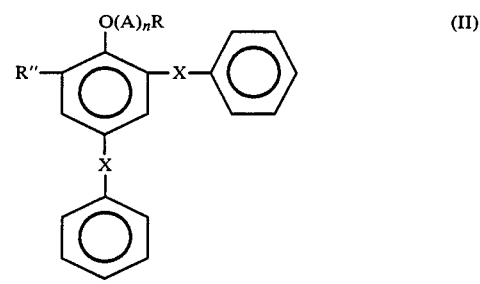

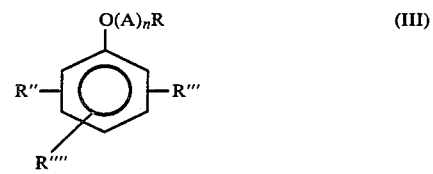

and

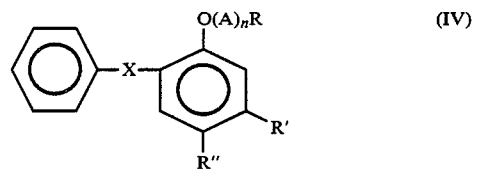

wherein A is an oxyalkylene radical having 2 carbon atoms to 4 carbon atoms or mixtures thereof, R is acyl containing from 8 carbon atoms to 22 carbon atoms, R' is alkyl containing from 1 carbon atom to 10 carbon atoms, R'' is alkyl containing from 1 carbon atom to 22 carbon atoms, R''' is alkyl containing from 4 carbon atoms to 8 carbon atoms, and R'''' is R'' or R''', X is an alkylidene radical containing from 1 carbon atom to 3 carbon atoms, and n is an integer such that the molecular weight of the compound is between 500 and 2500 and with the proviso that either R'' or R''' is ortho to the oxygen in formula III.

2. The microemulsion of claim 1 wherein the compound is of formula IV, A is oxyethylene, R is an acyl radical containing from 16 to 20 carbon atoms, R' is methyl, R" is C₄H₉—, and X is

3. The microemulsion of claim 1 wherein the compound is of formula IV, A is a mixture of oxyethylene and an oxyalkylene group containing 3 to 4 carbon atoms, R is an acyl radical containing from 16 to 20 carbon atoms, R' is methyl, R" is C₄H₉—, and X is

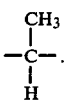

4. The microemulsion of claim 1 wherein the compound is of formula I, A is oxyethylene, R is an acyl radical containing from 16 to 20 carbon atoms and X is

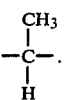

5. The microemulsion of claim 1 wherein the compound is of formula I, A is a mixture of oxyethylene and an oxyalkylene group containing 3 to 4 carbon atoms, R is an acyl radical containing from 16 to 20 carbon atoms and X is

6. The microemulsion of claim 1 wherein the compound is of formula II, A is oxyethylene, R is an acyl radical containing from 16 to 20 carbon atoms, R" is C₄H₉—,
and X is

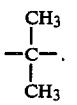

7. The microemulsion of claim 1 wherein the compound is of formula II, A is a mixture of oxyethylene and an oxyalkylene group containing 3 to 4 carbon atoms, R is an acyl radical containing from 16 to 20 carbon atoms, R" is C₄H₉—, and X is

8. The microemulsion of claim 1 wherein the compound is of formula III, A is oxyethylene, R is an acyl group containing from 16 to 20 carbon atoms, R" is C₄H₉—, R'" is C₈H₁₇— and R"" is C₈H₁₂— or C₄H₉— or a mixture of such compounds.

9. The microemulsion of claim 1 wherein the compound is of formula III, A is a mixture of oxyethylene and an oxyalkylene group containing 3 to 4 carbon atoms, R is an acyl group containing from 16 to 20 carbon atoms, R" is C₄H₉—, R'" is C₈H₁₇— and R"" is C₈H₁₂— or C₄H₉— or a mixture of such compounds.

10. The microemulsion of claim 1 including about 1 to 40 percent oil.

11. The microemulsion of claim 10 including about 1 to 40 percent alkali metal salt of a phosphate ester of an alkoxylated aliphatic alcohol having from 10 to 18 carbon atoms.

12. The microemulsion of claim 11 wherein said oil is tridecylstearate.

13. The microemulsion of claim 11 wherein the compound is of formula IV, A is oxyethylene, R is an acyl radical containing 16 to 20 carbon atoms, R' is methyl, R" is C₄H₉—, and X is

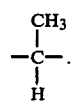

and said surfactant is an alkali metal salt of the phosphate ester of an alkoxylated 10 to 18 carbon atom aliphatic alcohol which is alkoxylated with a mixture of ethylene oxide and propylene oxide in a ratio of 90:10 to 10:90 and having a molecular weight of 500 to 1500.

14. The microemulsion of claim 11 wherein the compound is of formula IV, A is a mixture of oxyethylene and an oxyalkylene group containing 3 to 4 carbon atoms, R is an acyl radical containing 16 to 20 carbon atoms, R' is methyl, R" is C₄H₉—, and X is

and said surfactant is an alkali metal salt of the phosphate ester of an alkoxylated 10 to 18 carbon atom aliphatic alcohol which is alkoxylated with a mixture of ethylene oxide and propylene oxide in a ratio of 90:10 to 10:90 and having a molecular weight of 500 to 1500.

15. The microemulsion of claim 11 wherein the compound is of formula I, A is oxyethylene, R is an acyl radical containing 16 to 20 carbon atoms and X is

and said surfactant is an alkali metal salt of the phosphate ester of an alkoxylated 10-18 carbon atoms aliphatic alcohol which is alkoxylated with a mixture of ethylene oxide and propylene oxide in a ratio of 90:10 to 10:90 and having a molecular weight of 500 to 1500.

16. The microemulsion of claim 11 wherein the compound is of formula I, A is a mixture of oxyethylene and a oxyalkylene group containing 3 to 4 carbon atoms, R is an acyl radical containing from 16 to 20 carbon atoms and X is

and said surfactant is an alkali metal salt of the phosphate ester of an alkoxylated 10 to 18 carbon atom aliphatic alcohol which is alkoxylated with a mixture of ethylene oxide and propylene oxide in a ratio of 90:10 to 10:90 and having a molecular weight of 500 to 1500.

17. The microemulsions of claim 11 wherein the compound is of formula II, A is oxyethylene, R is an acyl containing 16 to 20 carbon atoms, R" is $C_4H_9$ and X is

and said surfactant is an alkali metal salt of the phosphate ester of an alkoxylated 10-18 carbon atom aliphatic alcohol which is alkoxylated with a mixture of ethylene oxide and propylene oxide in a ratio of 90:10 to 10:90 and having a molecular weight of 500 to 1500.

18. The microemulsion of claim 11 wherein the compound is of formula II, A is a mixture of oxyethylene and an oxyalkylene group containing 3 to 4 carbon atoms, R is an acyl radical containing from 16 to 20 carbon atoms, R" is $C_4H_9$— and X is

and said surfactant is an alkali metal salt of the phosphate ester of an alkoxylated 10 to 18 carbon atom aliphatic alcohol which is alkoxylated with a mixture of ethylene oxide and propylene oxide in a ratio of 90:10 to 10:90 and having a molecular weight of 500 to 1500.

19. The microemulsion of claim 11 wherein the compound is of formula III, A is oxyethylene and R is an acyl group containing 16 to 20 carbon atom, R" is $C_4H_9$—, R'" is $C_8H_{17}$— and R"" is $C_8H_{17}$— or $C_4H_9$— or a mixture of both compounds and said surfactant is the potassium salt of the phosphate ester of an alkoxylated 10-18 carbon atom aliphatic alcohol which is alkoxylated with a mixture of ethylene oxide and propylene oxide in a ratio of 90:10 to 10:90 and having a molecular weight of 500 to 1500.

20. The microemulsion of claim 11 wherein the compound is of formula III, A is a mixture of oxyethylene and an oxyalkylene group containing 3 to 4 carbon atoms, R is an acyl radical containing from 16 to 20 carbon atoms, R" is $C_4H_9$—, R'" is $C_8H_{17}$— and R"" is $C_8H_{17}$— or $C_4H_9$— or a mixture of both compounds and said surfactant is the potassium salt of the phosphate ester of an alkoxylated 10 to 18 carbon atom aliphatic alcohol which is alkoxylated with a mixture of ethylene oxide and propylene oxide in a ratio of 90:10 to 10:90 and having a molecular weight of 500 to 1500.

* * * * *